United States Patent [19]

Kurihara et al.

[11] 4,341,563
[45] Jul. 27, 1982

[54] PROTECTIVE COATING COMPOSITIONS

[75] Inventors: Kozo Kurihara; Toshio Fukazawa; Izuo Ichikawa; Yoshihiko Ikegami; Naohiko Fukiyama; Masaru Ikeda, all of Tokyo, Japan

[73] Assignee: Sankyo Company Limited, Tokyo, Japan

[21] Appl. No.: 148,172

[22] Filed: May 8, 1980

Related U.S. Application Data

[63] Continuation of Ser. No. 961,559, Nov. 17, 1978, abandoned, which is a continuation-in-part of Ser. No. 834,848, Sep. 20, 1977, abandoned.

[51] Int. Cl.$^3$ .......................... A61K 9/30; A61K 9/36; A61K 9/42; C08L 1/28
[52] U.S. Cl. .................................... 106/171; 106/191; 106/206; 106/207; 106/219; 106/230; 106/231; 424/33; 424/35; 424/38
[58] Field of Search ................. 106/171, 10, 206, 207, 106/191, 170, 219, 230; 424/35, 38, 33; 260/23 R, 23 AR, 23 P, 28.5 R

[56] References Cited

U.S. PATENT DOCUMENTS

| | | | |
|---|---|---|---|
| 3,406,031 | 10/1968 | Lee | 424/35 |
| 3,438,797 | 4/1969 | Biddle | 424/38 |
| 3,803,111 | 4/1974 | Munroe et al. | 260/31.2 R |
| 3,836,371 | 9/1974 | Kokoszka | 106/10 |
| 3,926,951 | 12/1975 | Lindenfors | 106/197 R |
| 3,960,757 | 6/1976 | Morshita | 424/33 |
| 4,013,475 | 3/1977 | Liebowitz et al. | 106/271 |

FOREIGN PATENT DOCUMENTS 1417326 10/1968 Fed. Rep. of Germany ........ 424/38

OTHER PUBLICATIONS

Warth, "The Chemistry and Technology of Waxes", pp. 80, 163, 1956.
Schwartz et al., "Surface Active Agents and Detergents", vol. II, Interscience Publishers, Inc., N.Y., 1958, p. 479.

*Primary Examiner*—Allan Lieberman
*Attorney, Agent, or Firm*—Toren, McGeady and Stanger

[57] ABSTRACT

Protective coating composition which comprises dispersed fine particles of one or more of compounds selected from a metal salt of a higher fatty acid, a higher fatty acid having a melting point of 40°–90° C., and a wax having a melting point of 40°–90° C. in an aqueous solution of a water-soluble film base and a surface-active agent having an HLB value of about 1.7 to 8.6 or silicon oil.

13 Claims, 1 Drawing Figure

PROTECTIVE COATING COMPOSITIONS

CROSS REFERENCE TO RELATED APPLICATIONS

This is a continuation of application Ser. No. 961,559, filed Nov. 17, 1978, now abandoned which, in turn, is a continuation-in-part of application Ser. No. 834,848, filed Sept. 20, 1977, now abandoned.

BACKGROUND OF THE INVENTION

1. Field of the Invention

The present invention relates to a composition of coating solution using water as a main solvent, which is employed for applying a coating film which is moisture proof to a solid preparation.

2. Description of the Prior Art

More particularly, the invention relates to a coating composition which yields a coating having good luster and smooth taste as well as being moisture proof, which has a masking effect preventing the active ingredient in the preparation from being released in the mouth before swallowing, and which has a definite and suitable delay of dissolution ensuring rapid release of the content after swallowing.

To the tablet, pill and granule is usually applied a coating by using various kinds of high-molecular compounds as coating material, in order to prevent degeneration or decomposition of the active ingredient due to hygroscopic or other cause either in the process of manufacture or during the storage time until it is administered. As high-molecular compounds employed for this purpose are known shellac, cellulose acetate phthalate (CAP), methyl vinyl pyridine.methyl acrylate.methacrylic acid copolymer (MPM), ethyl cellulose (EC), polyvinyl acetal diethylaminoacetate (AEA) and the like.

In performing the coating with such high-molecular compounds as mentioned above, they are generally dissolved in an organic solvent with high volatility and then the resulting solution is used for spray-coating. In this case, the organic solvent is discharged into the air along with the exhaust air to become a source of air-polution, and a provision is therefore required to wash the exhaust air with water to trap the organic solvent. Furthermore, in order to keep a good working environment, a lot of expense is required for air-conditioning equipment, antiexplosion provision for electric appliances and others, and the cost of the solvent employed is by no means negligible.

Such problems seem to be solved by using water as a coating solvent, but they have still remained unsettled for various reasons. The first reason is the absence of water-soluble film bases which are highly moisture proof, and the second is that, when an aqueous coating solution is employed, the moisture penetrates into the preparation during the process of spraying.

There is already known a liquid coating composition which comprises blending stearic acid or the like for imparting moisture proof properties to a water-soluble film base having poor moisture resistance in itself, such as hydroxypropyl cellulose (HPC), hydroxypropyl methyl cellulose (HPMC), an organic acid salt of AEA or the like. In this case, however, there is the disadvantage that the use of organic solvent becomes inevitable for dissolving stearic acid.

One of the most important requisites for the coated solid medicine orally administered is to have a masking property preventing the active ingredient having a pungent taste and unpleasant smell from being released out of the preparation into the mouth. Such a property of the coating film must be compatible with a property to rapidly release the content of the preparation after swallowing so as not to lower the bioavailability of medicine. Such a characteristic can be estimated in the dissolution test of the preparation by observing the delay of dissolution, which means a complete prevention to release the active ingredient for a definite time, and the subsequent rapid release. The delay of dissolution is usually sufficient if it is 1 to 5 minutes, and it is desirable that is be freely regulated by selecting the conditions in preparing the coating film.

In view of such a present situation, the present inventors have earnestly attempted to solve these problems and have succeeded in preparing an improved coating film which fully satisfies all of the above-mentioned problems.

SUMMARY OF THE INVENTION

The coating composition of the present invention comprises, as explained in detail below, dispersed fine particles of one or more kinds of compounds selected from the group consisting of (1) the metal salt of a higher fatty acid, (2) a higher fatty acid having a melting point in the range of 40°–90° C. and (3) a wax in an aqueous solution of one or more kinds of water-soluble film bases prepared by adding the surface active agent having an HLB value of from about 1.7 to 8.6, and/or silicon oil to the above aqueous solution. Of course, two or more kinds of compounds from each of the groups (1), (2) and (3) may be selected and dispersed together.

A solid preparation can be coated with an excellent moisture proof and protective film which is formed by spraying the composition of the present invention onto the said preparation in a conventional manner. The coated preparation thus obtained can be further coated with a coating layer of sugar, gelatin, or the like. However, this coated preparation itself possesses a glossy and smooth surface good enough to be used commerically.

BRIEF DESCRIPTION OF THE DRAWING

The drawing is a graph of the variation in release of active ingredients with time for different coated tablets.

DESCRIPTION OF THE PREFERRED EMBODIMENT

Figure 1:
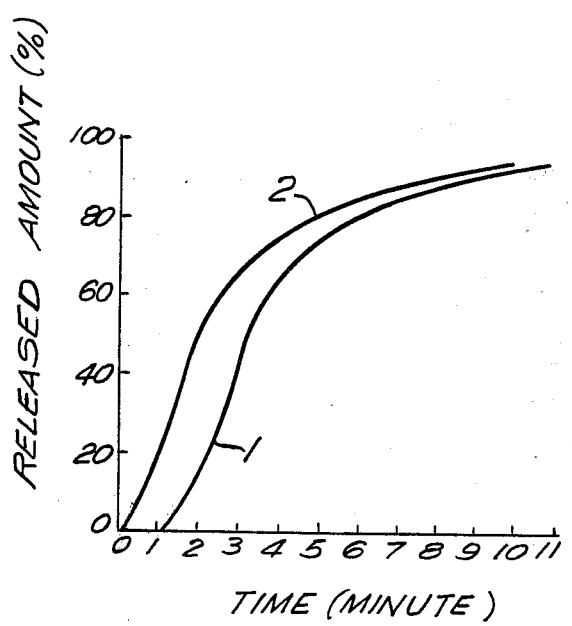

Surfactants are generally known for use as emulsifiers, wetting agents, or dispersing agents and surfactants having an HLB value of not less than about 10 are usually employed for said purposes when water is used as the medium. Moreover, it is generally considered in the art that the action of a surfactant on a hydrophobic material in an aqueous medium is to make the surface of the hydrophobic material more hydrophilic due to the agglomeration of the surfactant on the interface between the hydrophobic material and the water.

Applicants have discovered, however, that by the use of a specific combination of a hydrophobic material, i.e., a fatty acid or wax, in a water-soluble film base with a specific surfactant which has an HLB value of from about 1.7 to 8.6 or silicon oil, and water, a remarkable increase in the hydrophobic properties or the moisture proof properties of the resulting coating film can be obtained. This result contradicts the expected result of loss of hydrophobic properties when a surfactant is used.

As shown in the following table, surfactants which have an HLB value of not less than 10, do not have the effect of improving the moisture proof properties of a composition in accordance with the present invention whereas those having an HLB value of not more than 10, provide improved moisture proof properties particularly as the HLB value decreases. Thus, the action of the surfactant in the present composition is not that of a wetting, emulsifying or dispersing agent for which such materials are normally used. Thus, by use of the present composition, improved moisture proof properties and masking effects can be obtained without release of the active ingredient in the mouth before swallowing. Moreover, rapid dissolution does occur so as to rapidly release the active ingredient after swallowing despite the presence of the hydrophobic properties.

The higher fatty acids preferably used are those having a melting point at a range of 40°–90° C., such as lauric acid, myristic acid, palmitic acid, stearic acid or the like, and those having a melting point at a range of 50°–70° C. are more preferable.

As the wax, hydrogenated vegetable oils having a melting point at a range of 40°–90° C. may be equally employed, besides carnauba wax, whale wax, beeswax, white beeswax and the like.

Among the metal salts of higher fatty acids, those which are available as fine particles, such as magnesium stearate or calcium stearate are preferable. The fine particle mentioned here means that having a size of less than several microns, and the dispersed particles become more preferable as they become smaller.

The effect of lowering the moisture permeability is not recognized at all in a high-molecular coating film blended with the surface active agent, alone while said

TABLE A

Effect of H.L.B.[1] of Surface Active Agent on Moisture Permeability

| Used Surface Active Agent | | H.L.B. of Surface Active Agent | Moisture Permeability of Film[2] ($H_2O.g/m^2/day$)[3] |
|---|---|---|---|
| No. 1 | Sorbitan trioleate | 1.7 | 170 |
| No. 2 | Sorbitan monooleate | 4.3 | 235 |
| No. 3 | Sorbitan monostearate | 4.7 | 198 |
| No. 4 | Sorbitan monopalmitate | 6.7 | 213 |
| No. 5 | Sorbitan monolaurate | 8.6 | 175 |
| No. 6 | Sorbitan trioleate + polyoxyethylene sorbitan monostearate (mixing ratio = 0.45:0.55) | 9.0 | 343 |
| No. 7 | Polyoxyethylene sorbitan trioleate | 11.0 | 427 |
| No. 8 | Sorbitan trioleate + polyoxyethylene sorbitan monostearate (mixing ratio = 0.15:0.85) | 13.0 | 340 |
| No. 9 | Polyoxyethylene sorbitan monostearate | 14.9 | 521 |
| No. 10 | Polyoxyethylene sorbitan monopalmitate | 15.6 | 434 |
| No. 11 | Polyoxyethylene sorbitan monolaurate | 16.7 | 579 |

[1]Hydrophile-Lypophile Balance
[2]Composition of Film (w/w %)
HPMC 76.9
Beeswax 15.4
Surface Active Agent 7.7
[3]JIS cup method (Z-0208-1973), 40° C. × 90% RH, values at 100μ of film thickness The water-soluble film bases employed in the present invention are not only an essentially water-soluble high-molecular compound such as HPC or HPMC, but also a compound which can be made water-soluble such as AEA dissolved in an acidic aqueous solution; or CAP, shellac, or hydroxypropyl methyl cellulose phthalate (HPMCP) dissolved in an alkaline aqueous solution. Other representative examples of water-soluble film bases are methyl cellulose, hydroxyethyl cellulose, sodium carboxymethylcellulose, polyvinyl alcohol, polyvinylpyrrolidone, an organic acid salt of AEA, sodium hydroxypropyl methyl cellulose phthalate, sodium alginate, a copolymer of sodium methyl methacrylate and methacrylic acid, sodium cellulose acetate phthalate or the like.

Among these compounds, however, HPC is inferior to some degree in the ability of forming a coating film as compared with other high-molecular compounds. Among organic acid salts of AEA, fumarate is preferable with respect to the toxicity, taste and solubility. An aqueous solution of sodium alginate prepared by partial hydrolysis having a lowered viscosity, is preferably employed as a coating solution because the concentration of sodium alginate can be increased in it. A coating film of sodium cellulose acetate phthalate is not preferable because of a tendency to release acetic acid during the storage.

effect appears in a film jointly blended with the wax, the higher fatty acid and/or the metal salt of higher fatty acid together with the surface active agent.

Any surface active agent may be employed if an HLB value thereof is in the range of about 1.7–8.6. As the surface active agents are preferable the fatty acid esters of sorbitan, polyoxyethylene sorbitan and sucrose. The most preferable examples are sorbitan trioleate, sorbitan monolaurate, polyoxyethylene sorbitan monooleate, sorbitan monooleate, sorbitan monostearate, sorbitan monopalmitate and the fatty acid ester of sucrose. If desired, two or more kinds of surface active agents may be used provided that an HLB value thereof should be in the range of about 1.7–8.6.

Further, if desirable, food pigment, coloring agent such as titanium oxide, plastisizer such as polyethylene glycol, or perfume may be added. In order to inhibit the propagation of germs preservatives such as, parabens may be added to the present composition.

The preparation of the coating solution is carried out by dispersing fine particles of the wax, the higher fatty acid and/or the metal salt of higher fatty acid with a suitable dispersing device into an aqueous solution of the high-molecular compound, or into an aqueous solution prepared by adding the surface active agent and/or silicon oil to an aqueous solution of the high-molecular compound. When the wax and the higher fatty acid are employed in a massive state, the aqueous solution of the high-molecular compound is heated until they are fused and the mixture is then dispersed using a suitable device. There are some high-molecular compounds which gel on heating, but such gelatin does not interfere at all with the dispersion of the wax and the fatty acid.

As to the concentration of the solid material in the coating solution, there is no limitation. However, the results obtained by the coating test performed under various conditions using water as a solvent, indicate, when the rate of coating of the solid material is small per unit surface area of the preparation, the coating film formed is apt to be peeled away, and, when a coating solution with too high concentration is employed, the film is not formed uniformly and exhibits a rugged surface.

The mixing ratio of the wax, the higher fatty acid and/or the metal salt of higher fatty acid to the high-molecular compound is generally not limited, but too small content of the wax, the higher fatty acid and/or the metal salt of higher fatty acid makes the luster and smooth taste worse, while too much reduces the film-forming ability and promotes the occurrence of wrinkle and seam. The amount of the surface active agent employed is usually not limited, but excess amounts should be avoided, because it sometimes adversely affects the moisture permeability. There is also no limitation in the amount of silicon oil employed, but too much use should be avoided, because it sometimes lowers the adhesive power of the film to the tablet.

It is naturally feasible to use jointly two or more kinds of compounds selected from any one or each of the water-soluble high-molecular compound, the wax, the higher fatty acid, the metal salt of higher fatty acid, the surface active agent and silicon oil.

The coating film formed with the composition of the present invention has both the moisture proof property and the dissolution property, and it can be used, of course, not only as the final coating but also as the under-coating.

The first characteristic of the present composition is to form a protective film with excellent moisture proof properties as mentioned above, and this fact is shown in Table 1 and Table 2 as the effect of various coating compositions. The effect of use of the surface active agent together with the wax is shown in Table 3.

TABLE 2

| Effect of Various Coating Compositions (w/w %) | | | | | | | | |
|---|---|---|---|---|---|---|---|---|
| HPMC | 100 | 83.3 | 83.3 | 98.0 | 83.3 | 82.0 | 82.0 | 82.0 |
| Beeswax | 0 | 16.7 | 0 | 0 | 8.35 | 16.4 | 0 | 16.4 |
| Stearic acid | 0 | 0 | 16.7 | 0 | 8.35 | 0 | 16.4 | 0 |
| Sorbitan trioleate | 0 | 0 | 0 | 2.0 | 0 | 1.6 | 1.6 | 0 |
| Silicon oil KS-66 *1 | 0 | 0 | 0 | 0 | 0 | 0 | 0 | 1.6 |
| Solvent employed | water | water | water | water | water | water | water | water |
| Moisture permeability ($H_2O \cdot g/m^2$/day) *2 | 550 | 355 | 354 | 693 | 391 | 251 | 245 | 301 |

*1 Available from Shin-Etsu Chemical Co., Ltd.
*2 The same as described in Table 1

The measurement of moisture permeability in Table 1 was performed according to the JIS cup method. As clearly seen in Table 1, the coating film formed from the indicated Compositions exhibited superior moisture proof as compared with those of HPMC and HPC, and some of the indicated Compositions were found to produce films with the same level of moisture proof properties as that of the water-insoluble and moisture proof coating film (for example, AEA). As shown in Table 2, the coating film composed of the water-soluble high-molecular compound and the surface active agent did not provide any improvement as compared with that of the water-soluble high-molecular compound alone. In other words, addition of the surface active agent alone rather deteriorates the quality of the coating film composed of the water-soluble high-molecular compound. Unexpectedly, however, the addition of the surface active agent together with the wax, the metal salt of higher fatty acid and/or the higher fatty acid to the water-soluble high-molecular coating film was found to remarkably lower the moisture permeability of the film, and impart to the film a definite delay of dissolution as defined above, while maintaining the improving effect for the luster and smooth taste which is given with the wax, the metal salt of higher fatty acid and/or the higher fatty acid.

Moreover, it was more preferably found that the active ingredient was released very rapidly from the coated preparation after a definite delay of dissolution. The delay of dissolution was found to be easily and

TABLE 1

| Component | Control 1 *1 | Control 2 *2 | Control 3 *2 | Composition 1 | Composition 2 | Composition 3 | Composition 4 | Composition 5 | Composition 6 |
|---|---|---|---|---|---|---|---|---|---|
| AEA | 10 | | | | 2.1 | 4.2 | 2.1 | | |
| HPMC | | 10 | | 7.0 | 6.4 | 4.3 | 6.4 | | |
| HPC | | | 10 | | | | | 7.0 | 7.0 |
| Fumaric acid | | | | | 0.2 | 0.4 | 0.2 | | |
| Stearic acid | | | | 3.0 | 1.5 | 3.0 | | 3.0 | 3.0 |
| Magnesium stearate | | | | | | | 1.5 | | |
| Polyoxyethylene sorbitan monooleate | | | | | | | 0.3 | 0.8 | |
| Water | | q.s. | q.s. | q.s. | q.s. | q.s. | q.s. | q.s. | q.s. |
| Ethanol | 45 | | | | | | | | |
| Acetone | 45 | | | | | | | | |
| Total | 100 | 100 | 100 | 100 | 100 | 100 | 100 | 100 | 100 |
| Moisture permeability ($H_2O \cdot g/m^2$/day)*3 | 120 | 550 | 406 | 84 | 203 | 59 | 239 | 95 | 111 |

*1 Water-insoluble and moisture proofing coating film
*2 Water-soluble film base
*3 JIS cup method (Z-0208-1973), 40° C. × 90% RH, values at 100μ of film thickness freely regulated upon the kind and mixing ratio of the wax, the higher fatty acid, the metal salt of higher fatty acid and/or the surface active agent, as well as the amount to be coated per unit surface area of the preparation. Thus, the second characteristic of the present composition lies in having not only the excellent moisture proof and dissolution property, but also the definite and suitable delay of disintegration and dissolution. Therefore, the tablet with bitter taste, when coated with the composition of the invention, is imparted with a favorable smooth taste and the bitterness is concealed not to be felt on keeping it in the mouth for 1 minute rolling on the tongue.

The third characteristic of the composition of the invention is a remarkable improvement in the workability of coating operations. In the case of spray-coating of an aqueous solution of the water-soluble film base such as HPMC or HPC on the solid preparation, it is difficult to form a good film, since mutual cohesion of the preparation and adhesion of the preparation onto the wall of coating pan take place. When coated with the present composition, however, such an adhesion or cohesion was not observed in spite of using water as solvent and a good film is easily obtained with the improved workability.

The protective coating liquid composition in the present invention may be spray-dried to a powder or granule form, which can be dispersed in water and applied at the use. This dispersion can be easily carried out without heating. The coating of the liquid thus dispersed can be performed in the same manner as done before spray-drying, and no difference was observed in the moisture permeability which is an index of the moisture proof between films formed with the liquids before and after spray-drying.

The following Examples are given to illustrate the present invention.

REFERENCE EXAMPLE 1

Preparation of coating solution

Ten parts of 7.2% (by weight) aqueous solution of HPMC was warmed to 70° C. on a water bath. On the other hand, 3 parts of stearic acid was fused by heating on a water bath and the fused compound was poured, keeping the temperature at 70° C., into the above-described HPMC solution under warming with vigorous stirring using TK Homomixer (supplied from Tokushu Kika Kogyo Co., Ltd.). After 5 minutes, heating was discontinued and the mixture was cooled to room temperature with water. Thirteen parts of the creamy substance thus obtained was mixed with 87 parts of 7.2% aqueous solution of HPMC to prepare a composition of coating solution. The final composition is as follows.

| HPMC | 7.0% (w/w) |
|---|---|
| Stearic acid | 3.0 |
| Water | 90 |

Coating

In a small apple-shaped pan was placed 800 g of tablets (150 mg/T: Disintegration time, 1 minute) composing of 15 parts of anhydrous crystalline glucose, 13 parts of potato starch, 1.5 parts of magnesium stearate and 120.5 parts of lactose, and spray-coated with the coating solution of the above-described composition according to the usual method. The spray was carried out intermittently until the increase of mean weight of the tablet amounted to 7.5 mg/T under the conditions of the coating solution of room temperature, drying air of 75° C. and the temperature of tablet at 50° C. Thereafter, an additional drying was performed for 10 minutes to obtain coated tablets.

The tablet thus obtained had a smooth and lustrous surface, and the disintegration time was estimated to be 6 minutes in the first solution specified under the Japanese Pharmacopeia, 8th Edition (hereinafter abbreviated as JP, VIII) and 7 minutes in water at 37° C. The loss of weight drying was 3.3% in the uncoated tablet and 3.2% in the coated one. The increase of moisture content in the tablet was not recognized in the coating process.

EXAMPLE 1

Preparation of coating solution

To a solution of 0.2 parts of fumaric acid in 89 parts of water was dissolved with stirring 2.1 parts of AEA, to which 6.4 parts of HPMC and 0.3 parts of polyoxyethylene sorbitan monooleate were added and dissolved. Thereafter, 1.5 parts of magnesium stearate was added to the solution and suspended with vigorous agitation to obtain a coating composition.

Coating

Using a coating solution of the above-described composition, the coated tablet was prepared under the same conditions as employed in Reference Example 1. The tablet thus obtained was slightly inferior in the luster of the surface, but was satisfactory for the purpose of protective coating. The disintegration time was 4 minutes in the first solution specified under JP, VIII and 7 minutes in water at 37° C.

REFERENCE EXAMPLE 2

Preparation of coating solution

To a solution of 0.2 parts of fumaric acid in 45 parts of water was dissolved 2.1 parts of AEA. To the above solution warmed to about 70° C. was then added 1.5 parts of stearic acid which was previously fused to about 70° C. in a separate vessel, and then the mixture was agitated vigorously for 5 minutes and cooled to room temperature to obtain the Solution I.

To the Solution II prepared by dissolving 6.4 parts of HPMC in 43 parts of water was added and mixed with stirring 48.8 parts of the Solution I, and the total amount of the mixture was made 100 parts by adding 1.8 parts of water to yield a coating solution. The final composition of the solution is as follows:

| HPMC | 6.4% (w/w) |
|---|---|
| AEA | 2.1 |
| Fumaric acid | 0.2 |
| Stearic acid | 1.5 |
| Water | 89.8 |

Coating

In a large-sized apple-shaped pan was placed 1.5 kg of compound cold tablet ("New LuLu Gold", tradename of Sankyo Co., Ltd.) (260 mg/T: Disintegration time, 14 minutes in the first solution specified under JP, VIII), together with 50 kg of placebo tablets, and spray-coated with the coating solution with the above-described composition by a conventional manner. The spray was carried out continuously until the increase of mean weight of the tablet amounted to 8.0 mg/T under the conditions of the coating solution of room temperature, drying air of 80° C. and the temperature of tablet at 50° C. An additional drying was then performed for 10 minutes to obtain coated tablets.

The tablet thus obtained had a smooth and lustrous surface, and the disintegration time was found to be 16 minutes in the first solution described in JP, VIII and 16 minutes in water at 37° C. The weight loss on drying was 3.0% in the uncoated tablet and 2.9% in the coated one, no moisture penetration being observed during the coating process.

EXAMPLE 2

In a coating apparatus was placed and spray-coated 11 kg of tablet with $\phi=6.5$ mm and R=8.0 mm, each having a weight of 100 mg and containing 50 mg of 2-(2-isopropylindan-5-yl)propionic acid. The composition of coating solution is described in Table 3, and the results from the test with the coated tablet are shown in Table 4.

TABLE 3

| Composition of Coating Solution (w/w %) | | | | |
|---|---|---|---|---|
| Solution No. | A | B | C | D |
| HPMC | 10 | 10 | 10 | 10 |
| White beeswax | 0 | 2 | 2 | 2 |
| Sorbitan trioleate | 0 | 0 | 0.2 | 0.2 |
| Water | 90 | 88 | 87.8 | 10 |
| Ethanol | 0 | 0 | 0 | 77.8 |

TABLE 4

| | Results of Test | | | | | | | | |
|---|---|---|---|---|---|---|---|---|---|
| Solution No. | — | A | | B | | C | | D | |
| Amount of solid material coated (mg/T) | 0 | 3.6 | 4.8 | 3.6 | 4.8 | 3.6 | 4.8 | 3.6 | 4.8 |
| Luster *1 | | X | X | X | | | | | |
| Taste *1 | | X | X | X | | | | | |
| Masking effect *2 | | X | X | Δ | Δ | | | | |
| Dissolution *3 (min) tl | 0.1 | 0.6 | 1.0 | 0.8 | 1.1 | 1.3 | 3.5 | 1.5 | 4.1 |
| $t_{50}$ − tl | 0.1 | 1.0 | 1.3 | 1.2 | 1.2 | 1.1 | 1.1 | 1.1 | 1.1 |

Note (the same meanings will be applied in the following Examples):
*1 X: Bad. Δ: Slightly bad. : Good.
*2 Degree of tasting the characteristic bitterness with astringency of the active ingredient when the tablet is placed in the mouth for 1 minute rolling on the tongue.
X: strong taste. Δ: weak taste. : no taste at all.
*3 Dissolution test was performed according to the USP method. tl: Delay of dissolution. $t_{50}$: Time required for dissolving half amount of the active ingredient in one tablet.

EXAMPLE 3

In a coating vessel was placed 11 kg of tablet with $\phi=8.5$ mm and R=10.5 mm, each having a weight of 220 mg and containing 50 mg of 2-(2-isopropylindan-5-yl)propionic acid, and spray-coated until the solid material of coating film amounted to 4 mg/T. The composition of coating solution is shown in Table 5.

TABLE 5

| Composition of Coating Solution (w/w %) | |
|---|---|
| HPMC | 5 |
| White beeswax | 1 |
| Sorbitan trioleate | 0.1 |
| Water | 93.9 |

The tablet coated with the above composition had a good luster and smooth taste, and the characteristic bitterness with astringency of the active ingredient could not be tasted when it was placed in the mouth rolling on the tongue for 1 minute. The dissolution test was carried out with the uncoated tablet for comparison and the results obtained are shown in FIG. 1, in which a definite delay of dissolution is clearly seen for the tablet coated with the above composition, and the subsequent dissolution pattern is about the same as that of the uncoated tablet. This indicates that the coating does not affect on the releasing rate. For reference, the respective release curves of the tablet coated with the present composition and of the uncoated tablet are shown in FIG. 1, wherein "1" indicates the release curve of the tablet coated with the composition as defined in the above Example 3 and "2" indicates the corresponding curve of the uncoated tablet.

EXAMPLE 4

In a coating vessel was placed 11 kg of tablets with $\phi=8.5$ mm and R=10.5 mm, each having a weight of 220 mg and containing 3 mg of sodium benzoate, and spray-coated until the solid material of coating film amounted to 5.3 mg/T. The composition of coating solution is shown in Table 6. The results of test with the coated tablet are shown in Table 7.

TABLE 6

| Composition of Coating Solution (w/w %) | | | |
|---|---|---|---|
| Solution No. | A | B | C |
| HPMC | 12.5 | 12.5 | 12.5 |
| White beeswax | 2.5 | 0 | 0 |
| Carnauba wax | 0 | 2.5 | 0 |
| Stearic acid | 0 | 0 | 2.5 |
| Silicon oil | | | |
| KS 66 | 0.25 | 0.25 | 0.25 |
| Water | 84.75 | 84.75 | 84.75 |

TABLE 7

| | Results of Test | | | |
|---|---|---|---|---|
| Solution No. | Uncoated tablet | A | B | C |
| Ability of coating film formation | | X | | |
| Luster | | X | | |
| Taste | | X | | |
| Dissolution (min) tl | 0.1 | 1.3 | 1.4 | 1.4 |
| $t_{50}$ − tl | 0.4 | 0.4 | 0.4 | 0.4 |

EXAMPLE 5

In a coating vessel was placed 1 kg of tablets with $\phi=8.5$ mm and R=10.5 mm, each having a weight of 220 mg and containing 50 mg of 2-(2-isopropylindan-5-yl)propionic acid, and spray-coated until the solid material of coating film amounted to 4.3 mg/T. The composition of coating solution is described in Table 8. Firstly, HPMCP was dissolved in aqueous 0.1 N-NaOH solution and the wax and sorbitan trioleate were then added, and the mixture thus obtained was dispersed under heating with Homomixer.

The results of the test with the coated tablet are shown in Table 9.

TABLE 8

| | Composition of Coating Solution (w/w %) | |
|---|---|---|
| Solution No. | A | B |
| HPMCP | 10.0 | 10.0 |
| NaOH | 1.0 | 1.0 |
| White beeswax | 0 | 2.0 |
| Sorbitan trioleate | 0 | 0.2 |
| Water | 89.0 | 86.8 |

TABLE 9

| | Results of Test | | |
|---|---|---|---|
| Solution No. | A | B | Uncoated tablet |
| Ability of coating film formation | | | — |
| Luster | Δ | | X |
| Taste | Δ | | X |
| Dissolution (min) tl | 1.5 | 3.0 | 0.2 |
| $t_{50}$ − tl | 1.5 | 1.5 | 1.6 |

EXAMPLE 6

In a coating vessel was placed 1 kg of tablets with $\phi = 8.5$ mm and R = 10.5 mm, each having a weight of 220 mg and containing 10 mg of sodium benzoate, and spray-coated until the solid material of coating film amounted to 4.3 mg/T. The composition of coating solution is shown in Table 10. AEA and fumaric acid were dissolved in water and the wax and sorbitan trioleate were added, and the mixture thus obtained was dispersed under heating with Homomixer.

The results of the test with the coated tablet are shown in Table 11.

TABLE 10

| | Composition of Coating Solution (w/w %) | |
|---|---|---|
| Solution No. | A | B |
| AEA | 10.0 | 10.0 |
| Fumaric acid | 0.9 | 0.9 |
| White beeswax | 0 | 2.0 |
| Sorbitan trioleate | 0 | 0.2 |
| Water | 89.1 | 86.9 |

TABLE 11

| | Results of Test | | |
|---|---|---|---|
| Solution No. | A | B | Uncoated tablet |
| Ability of coating film formation | | | — |
| Luster | Δ | | X |
| Taste | X | | X |
| Dissolution (min) tl | 1.0 | 2.5 | 0.1 |
| $t_{50}$ − tl | 1.2 | 1.2 | 1.1 |

EXAMPLE 7

To a solution prepared by dissolving 12.5 parts of HPMC in 84.75 parts of water were added 2.5 parts of beeswax and 0.25 parts of sorbitan trioleate and the mixture was warmed to the fusing point of beeswax, and then dispersed with Homomixer. After cooling to below 40° C. under continuing the dispersing operation, the liquid thus dispersed was diluted three times with water, which was subsequently spray-dried with "Anhydro Spray Dryer" (made in Denmark) under the conditions of the drying air at 100°–110° C. and the spray disk operated at 45,000 rpm. The particle size of the spray-dried powder was about 100μ and, in an aqueous solution again prepared from the dried powder with a usual stirrer, the particle size of beeswax was the same order as in the solution before spray-drying. No difference before and after spray-drying was observed in the moisture permeability, which was 261 ($H_2O.g/m^2/day$), and nor in other qualities of coating films.

REFERENCE EXAMPLE 3

A coating solution was prepared according to the same composition and preparation method as in Reference Example 2, diluted twice with water, and then spray-dried with Anhydro Spray Dryer under the conditions of the drying air at 100°–110° C. and the spray disk operated at 45,000 rpm. The particle size of the spray-dried powder thus obtained was about 100μ, and the particle size of stearic acid in an aqueous solution again prepared from the powder was the same order as in the solution before spray-drying. The moisture permeability of the coating film was 190 ($H_2O.g/m^2/day$), the same order of the value as that of the film formed with the solution before spray-drying.

The tablet coated with the aqueous solution again prepared from the powder under the same conditions as described in Reference Example 2 exhibited a smooth and lustrous surface, and the disintegration time was 16 minutes in the first solution specified under JP, VIII, and 16 minutes in water at 37° C., the same values as those obtained when the coating solution before spray-drying was used.

What is claimed is:

1. An aqueous protective coating composition which comprises dispersed fine particles of a hydrophobic material selected from the group consisting of a metal salt of a higher fatty acid, a higher fatty acid having a melting point of 40°–90° C., a wax having a melting point of 40°–90° C. and mixtures thereof of a water-soluble film base containing an amount effective to increase the hydrophobic properties of the film resulting from said aqueous protective coating composition of a surface active agent having a total HLB value of about 1.7 to 8.6.

2. A composition according to claim 1 wherein said water-soluble film base is hydroxypropyl cellulose, hydroxypropyl methyl cellulose, a salt of polyvinyl acetal diethylaminoacetate, a salt of cellulose acetate phthalate, a salt of hydroxypropylmethyl cellulose phthalate, methyl cellulose, hydroxyethylcellulose, sodium carboxymethylcellulose, polyvinyl alcohol, polyvinylpyrrolidone, sodium alginate or a salt of an acrylate polymer.

3. A composition according to claim 2 wherein said salt of polyvinyl acetal diethylaminoacetate is a salt with a dibasic organic carboxylic acid and said salt of cellulose acetate phthalate, hydroxypropylmethyl cellulose phthalate or an acrylate polymer is an alkali metal salt or ammonium salt.

4. A composition according to claim 1 wherein said water-soluble film base is hydroxypropyl cellulose, hydroxypropylmethyl cellulose, a salt of polyvinyl acetal diethylaminoacetate or a salt of hydroxypropyl methyl cellulose phthalate.

5. A composition according to claim 1 wherein said metal salt of a higher fatty acid is an alkaline earth metal salt or ammonium salt of stearic acid.

6. A composition according to claim 1 wherein said metal salt of a higher fatty acid is magnesium or calcium stearate.

7. A composition according to claim 1 wherein said higher fatty acid is lauric acid, myristic acid, palmitic acid or stearic acid.

8. A composition according to claim 1 wherein said wax is carnauba wax, whale wax, beeswax, white beeswax or a hydrogenated vegetable oil.

9. A composition according to claim 1 wherein said surface active agent is a fatty acid ester of sorbitan.

10. A composition according to claim 1 wherein said surface active agent is sorbitan trioleate, sorbitan monooleate, sorbitan monostearate, sorbitan monopalmitate or sorbitan monolaurate.

11. A composition according to claim 1 wherein said surface active agent is a fatty acid ester of sorbitan, polyoxyethylene sorbitan or sucrose.

12. A protective coating composition which comprises dispersed fine particles of white beeswax in an aqueous solution of hydroxypropylmethyl cellulose and an amount effective to increase the hydrophobic properties of the film resulting from said aqueous protective coating composition of sorbitan trioleate having a total HLB value between about 1.7 to 8.6.

13. A protective coating composition which comprises dispersed fine particles of carnauba wax in an aqueous solution of hydroxypropyl methyl cellulose and an amount effective to increase the hydrophobic properties of the film resulting from said aqueous protective coating composition of sorbitan trioleate having a total HLB value between about 1.7 to 8.6.

* * * * *